(12) United States Patent
Danek et al.

(10) Patent No.: US 8,640,711 B2
(45) Date of Patent: Feb. 4, 2014

(54) METHOD FOR TREATING AN ASTHMA ATTACK

(75) Inventors: Christopher J. Danek, Santa Clara, CA (US); Bryan E. Loomas, Los Gatos, CA (US); Thomas M. Keast, Mountain View, CA (US); Michael D. Laufer, Menlo Park, CA (US)

(73) Assignee: Asthmatx, Inc., Sunnyvale, CA (US)

(*) Notice: Subject to any disclaimer, the term of this patent is extended or adjusted under 35 U.S.C. 154(b) by 176 days.

(21) Appl. No.: 12/964,678

(22) Filed: Dec. 9, 2010

(65) Prior Publication Data
US 2011/0079230 A1 Apr. 7, 2011

Related U.S. Application Data

(63) Continuation of application No. 12/727,156, filed on Mar. 18, 2010, now Pat. No. 8,161,978, which is a continuation of application No. 11/117,905, filed on Apr. 29, 2005, now Pat. No. 7,740,017, which is a continuation of application No. 09/999,851, filed on Oct. 25, 2001, now Pat. No. 7,027,869, which is a continuation-in-part of application No. 09/296,040, filed on Apr. 21, 1999, now Pat. No. 6,411,852, said application No. 11/117,905 is a continuation-in-part of application No. 09/436,455, filed on Nov. 8, 1999, now Pat. No. 7,425,212, and a continuation-in-part of application No. 10/232,909, filed on Aug. 30, 2002, now Pat. No. 7,556,624, which is a continuation of application No. 09/349,715, filed on Jul. 8, 1999, now Pat. No. 6,488,673, said application No. 09/999,851 is a continuation-in-part of application No. 09/535,856, filed on Mar. 27, 2000, now Pat. No. 6,634,363.

(51) Int. Cl.
*A61B 19/00* (2006.01)
*A61F 7/12* (2006.01)

(52) U.S. Cl.
USPC ............... 128/898; 607/42; 607/96; 607/101

(58) Field of Classification Search
USPC ........... 607/42, 96–105, 124; 606/27, 28, 32, 606/41, 50; 128/898
See application file for complete search history.

(56) References Cited

U.S. PATENT DOCUMENTS 612,724 A 10/1898 Hamilton
1,155,169 A 9/1915 Starkweather
(Continued)

FOREIGN PATENT DOCUMENTS

DE 19529634 A1 2/1997
EP 189329 A3 6/1987
(Continued)

OTHER PUBLICATIONS

An S. S., et al., "Airway smooth muscle dynamics: a common pathway of airway obstruction in asthma," European Respiratory Journal, 2007, 29 (5), 834-860.

(Continued)

*Primary Examiner* — Ahmed Farah
(74) *Attorney, Agent, or Firm* — Bookoff McAndrews, PLLC

(57) ABSTRACT

A method for treating the lung during an acute episode of reversible chronic obstructive pulmonary disease such as an asthma attack. The method comprises transferring energy to an airway wall of an airway such that a diameter of the airway is increased. The energy may be transferred to the airway wall prior to, during or after an asthma attack. The energy may be transferred in an amount sufficient to temporarily or permanently increase the diameter of the airway. The method may be performed while the airway is open, closed or partially closed.

16 Claims, 3 Drawing Sheets

(56) References Cited

U.S. PATENT DOCUMENTS

| | | |
|---|---|---|
| 1,207,479 A | 12/1916 | Bisgaard |
| 1,216,183 A | 2/1917 | Swingle |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | Leveen |
| 4,116,589 A | 9/1978 | Rishton |
| 4,129,129 A | 12/1978 | Amrine |
| 4,154,246 A | 5/1979 | LeVeen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,703 A | 6/1995 | Feiring |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |

(56) References Cited

U.S. PATENT DOCUMENTS

| | | |
|---|---|---|
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,660,175 A | 8/1997 | Dayal |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,979,456 A | 11/1999 | Magovern |
| 5,980,563 A | 11/1999 | Tu et al. |
| 5,984,917 A | 11/1999 | Fleischman et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |

(56) References Cited

U.S. PATENT DOCUMENTS

| | | |
|---|---|---|
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,090,104 A | 7/2000 | Webster, Jr. |
| 6,092,528 A | 7/2000 | Edwards |
| 6,102,886 A | 8/2000 | Lundquist et al. |
| 6,106,524 A | 8/2000 | Eggers et al. |
| 6,123,702 A | 9/2000 | Swanson et al. |
| 6,123,703 A | 9/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A | 11/2000 | Farley et al. |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,416,740 B1 | 7/2002 | Unger |
| 6,425,895 B1 | 7/2002 | Swanson et al. |
| 6,440,129 B1 | 8/2002 | Simpson |
| 6,442,435 B2 | 8/2002 | King et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin, Jr. et al. |
| 6,634,363 B1 | 10/2003 | Danek et al. |
| 6,635,056 B2 | 10/2003 | Kadhiresan et al. |
| 6,638,273 B1 | 10/2003 | Farley et al. |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,425,212 B1 | 9/2008 | Danek et al. |
| 7,542,802 B2 | 6/2009 | Biggs et al. |
| 7,556,624 B2 | 7/2009 | Laufer et al. |
| 7,740,017 B2 | 6/2010 | Danek et al. |
| 7,770,584 B2 | 8/2010 | Danek et al. |
| 8,088,127 B2* | 1/2012 | Mayse et al. ............... 606/41 |
| 8,161,978 B2* | 4/2012 | Danek et al. ............... 128/898 |
| 8,172,827 B2* | 5/2012 | Deem et al. ............... 604/506 |
| 8,226,638 B2* | 7/2012 | Mayse et al. ............... 606/32 |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0187430 A1 | 10/2003 | Vorisek |

(56) References Cited

U.S. PATENT DOCUMENTS

| | | |
|---|---|---|
| 2003/0236455 A1 | 12/2003 | Swanson et al. |
| 2004/0049175 A1 | 3/2004 | Speck et al. |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106339 A1 | 5/2007 | Errico et al. |
| 2007/0106348 A1 | 5/2007 | Laufer |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2007/0162085 A1 | 7/2007 | DiLorenzo |
| 2008/0004596 A1 | 1/2008 | Yun et al. |
| 2008/0097424 A1 | 4/2008 | Wizeman et al. |
| 2008/0132886 A1 | 6/2008 | Cohen et al. |
| 2008/0255642 A1 | 10/2008 | Zarins et al. |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0143705 A1 | 6/2009 | Danek et al. |
| 2009/0143776 A1 | 6/2009 | Danek et al. |
| 2009/0192505 A1 | 7/2009 | Askew et al. |
| 2009/0192508 A1 | 7/2009 | Laufer et al. |
| 2009/0306644 A1 | 12/2009 | Mayse et al. |
| 2010/0160906 A1 | 6/2010 | Jarrard |
| 2010/0204689 A1 | 8/2010 | Danek et al. |
| 2011/0118725 A1 | 5/2011 | Mayse et al. |
| 2011/0152855 A1 | 6/2011 | Mayse et al. |
| 2011/0257647 A1 | 10/2011 | Mayse et al. |

FOREIGN PATENT DOCUMENTS

| | | |
|---|---|---|
| EP | 286145 A2 | 10/1988 |
| EP | 280225 A3 | 3/1989 |
| EP | 286145 A3 | 10/1990 |
| EP | 282225 B1 | 6/1992 |
| EP | 908713 A1 | 4/1999 |
| EP | 908150 B1 | 5/2003 |
| EP | 768091 B1 | 7/2003 |
| EP | 1297795 B1 | 8/2005 |
| FR | 2659240 B1 | 7/1997 |
| JP | 59167707 A2 | 9/1984 |
| JP | 7289557 A2 | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | WO8911311 A1 | 11/1989 |
| WO | WO9502370 A3 | 1/1995 |
| WO | WO9510322 A1 | 4/1995 |
| WO | WO9604860 A1 | 2/1996 |
| WO | WO9610961 A1 | 4/1996 |
| WO | WO9732532 A1 | 9/1997 |
| WO | WO9733715 A1 | 9/1997 |
| WO | WO9737715 A1 | 10/1997 |
| WO | WO9740751 A1 | 11/1997 |
| WO | WO9844854 A1 | 10/1998 |
| WO | WO9852480 A1 | 11/1998 |
| WO | WO9856324 A1 | 12/1998 |
| WO | WO9903413 A1 | 1/1999 |
| WO | WO9858681 A3 | 3/1999 |
| WO | WO9913779 A2 | 3/1999 |
| WO | WO9932040 A1 | 7/1999 |
| WO | WO9934741 A1 | 7/1999 |
| WO | WO9944506 A1 | 9/1999 |
| WO | WO9945855 A1 | 9/1999 |
| WO | WO9964109 A1 | 12/1999 |
| WO | WO0051510 A1 | 9/2000 |
| WO | WO0062699 A3 | 10/2000 |
| WO | WO0103642 A1 | 1/2001 |
| WO | WO0232333 A1 | 4/2002 |
| WO | WO0232334 A1 | 4/2002 |
| WO | WO2007053230 A2 | 5/2007 |
| WO | WO2009082433 A2 | 7/2009 |
| WO | WO2009137819 A1 | 11/2009 |
| WO | WO2011056684 A2 | 5/2011 |
| WO | WO2011060200 A1 | 5/2011 |
| WO | WO2011060201 A1 | 5/2011 |
| WO | WO2011127216 A2 | 10/2011 |

OTHER PUBLICATIONS

Awadh N., et al., "Airway wall thickness in patients with near fatal asthma and control groups: assessment with high resolution computed tomographic scanning," Thorax, 1998, 53, 248-253.

Bel, et al., "Hot stuff": bronchial thermoplasty for asthma, American Journal of Respiratory and Critical Care Medicine, 2006, 173, 941-943.

Brown R. H., et al., "Effect of bronchial thermoplasty on airway distensibility," European Respiratory Journal, 2005, 26 (2), 277-282.

Brown R. H., et al., "In vivo evaluation of the effectiveness of bronchial thermoplasty with computed tomography," Journal of Applied Physiology, 2005, 98, 1603-1606.

Chhajed P., et al., "Will there be a role for bronchoscopic radiofrequency ablation?," J Bronchol, 2005, 12 (3), 184-186.

Co-pending U.S. Appl. No. 09/095,323.

Co-pending U.S. Appl. No. 09/244,173.

Cox G., et al., "Asthma Control during the Year after Bronchial Thermoplasty," The New England journal of medicine, 2007, 356 (13), 1327-1337.

Cox G., et al., "Asthma Intervention Research (AIR) Trial Evaluating Bronchial Thermoplasty™: Early Results, American Thoracic Society Annual Meeting," 2002, 1 page.

Cox G., et al., "Bronchial Thermoplasty for Asthma," American Journal of Respiratory and Critical Care Medicine, 2006, 173, 965-969.

Cox G., et al., "Bronchial Thermoplasty: Long-Term Follow-Up and Patient Satisfaction," Chest, 2004, 126 (4), 822s.

Cox G., et al., "Bronchial Thermoplasty: One-Year Update, American Thoracic Society Annual Meeting," Am J Respir Crit Care Med, 2004, 169, A313.

Cox G., et al., "Clinical Experience With Bronchial Thermoplasty for the Treatment of Asthma," Chest, 2003, 124, 106S.

Cox G., et al., "Development of a Novel Bronchoscopic Therapy for Asthma," Journal of Allergy and Clinical Immunology, 2003, 113 (2), S33.

Cox G., et al., "Early Clinical Experience with Bronchial Thermoplasty for the Treatment of Asthma, American Thoracic Society Annual Meeting," 2002, 1068.

(56) References Cited

OTHER PUBLICATIONS

Cox G., et al., "Impact of bronchial thermoplasty on asthma status: interim results from the AIR trial.European Respiratory Society Annual Meeting. Munich, Germany," 2006, 1 page.
Cox G., et al., "Radiofrequency ablation of airway smooth muscle for sustained treatment of asthma: preliminary investigations," European Respiratory Journal, 2004, 24, 659-663.
Danek C. J., et al., "Bronchial thermoplasty reduces canine airway responsiveness to local methacholine challenge, American Thoracic Society Annual Meeting," 2002, 1 page.
Danek C. J., et al., "Reduction in airway hyperresponsiveness to methacholine by the application of RF energy in dogs," J Appl Physiol, 2004, 97, 1946-1953.
Dierkesmann, et al., "Indication and Results of Endobronchial Laser Therapy," Lung, 1990, 168, 1095-1102.
Erle C. H., et al., "Botulinum toxin: a novel therapeutic option for bronchial asthma?," Medical Hypotheses, 2006, 66, 915-919.
Global Strategy for Asthma Management and Prevention, NIH, National Heart ,Lung and Blood Institute, 2002, 192 Pages Total.
Hogg J. C., "The Pathology of Asthma," APMIS, 1997, 105 (10), 735-745.
Ivanyuta O. M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
James, et al., "The Mechanics of Airway Narrowing in Asthma," Am. Rev. Respir. Dis., 1989, 139, 242-246.
Janssen L. J., "Asthma therapy: how far have we come, why did we fail and where should we go next?," Eur Respir J, 2009, 33, pp. 11-20.
Johnson S. R., et al., "Synthetic Functions of Airway Smooth Muscle in Asthma," Trends Pharmacol. Sci., 1997, 18 (8), 288-292.
Julian Solway M. D., et al., "Airway Smooth Muscle as a Target for Asthma Therapy," The New England journal of medicine, 2007, 356 (13), 1367-1369.
Kitamura S., "Color Atlas of Clinical Application of Fiberoptic Bronchoscopy," 1990, Year Book Medical Publishers, 17.
Kraft M., "The distal airways: are they Important in asthma?," European Respiratory, 1999, 1403-1417.
Laviolette, et al., "Asthma Intervention Research (Air) Trial: Early Safety Assessment of Bronchial Thermoplasty," Am J Respir Crit Care Med, 2004, 169, A314.
Leff, et al., Bronchial Thermoplasty Alters Airway Smooth Muscle and Reduces Responsiveness in Dogs: A Possible Procedure for the Treatment of Asthma, American Thoracic Society Annual Meeting 2002, 1 page.
Lombard, et al., "Histologic Effects of Bronchial Thermoplasty of Canine and Human Airways, American Thoracic Society Annual Meeting," 2002, 1 page.
Macklem P. T., "Mechanical Factors Determining Maximum Bronchoconstriction," European Respiratory Journal, 1989, 6, 516s-519s.
Martin N., et al, "Bronchial Thermoplasty for the Treatment of Asthma," Current Allergy and Asthma Reports, 2009, 9 (1), 88-95.
Mayse M. L., et al., "Clinical Pearls for Bronchial Thermoplasty," J Bronchol, 2007, 14 (2), 115-123.
Miller J. D., et al., "A Prospective Feasibility Study of Bronchial Thermoplasty in the Human Airway," 2005, 127, 1999-2006.
Miller J. D., et al., "Bronchial Thermoplasty Is Well Tolerated by Non-Asthmatic Patients Requiring Lobectomy, American Thoracic Society Annual Meeting," 2002, 1 page.
Netter F. H., "Respiratory System: A Compilation of Paintings Depicting Anatomy and Embryology, Physiology, Pathology, Pathophysiology, and Clinical Features and Treatment of Diseases,In The CIBA Collection of Medical Illustrations M.B. Divertie, ed., Summit: New Jerse," 1979, 7, 119-135.
Notice of final Rejection, Japanese Patent Application No. 2000-553172, dated Sep. 2, 2008, 5 pages.
PCT International search report for application No. PCT/US00/ 05412 mailed on Jun. 20, 2000, 2 pages.
PCT International search report for application No. PCT/US00/ 18197 mailed on Oct. 3, 2000, 1 page.
PCT International search report for application No. PCT/US00/ 28745 mailed on Mar. 28, 2001, 6 pages.
PCT International search report for application No. PCT/US01/ 32321 mailed on Jan. 18, 2002, 2 pages.
PCT International search report for application No. PCT/US98/ 03759 mailed on Jul. 30, 1998, 1 page.
PCT International search report for application No. PCT/US98/ 26227 mailed on Mar. 25, 1999, 1 page.
PCT International search report for application No. PCT/US99/ 00232 mailed on Mar. 4, 1999, 1 page.
PCT International search report for application No. PCT/US99/ 12986 mailed on Sep. 29, 1999, 1 page.
Peter K. Jeffery, "Remodeling in Asthma and Chronic Obstructive Lung Disease," American Journal of Respiratory and Critical Care Medicine, 2001, 164 (10), 13516.
Provotorov, et al., "The Clinical Efficacy of Treating Patients with Nonspecific Lung Disease by Using Low-energy Laser Irradiation and Intrapulmonary Drug Administration, ISSN: 0040-3660," Terapevticheskii Arkhiv (USSR), 1991, 62 (12), 18-23.
Rubin, et al., "Bronchial thermoplasty improves asthma status of moderate to severe perisstent asthmatics over and above current standard-of-care, American College of Chest Physicians," 2006, 2 pages.
Seow C. Y., et al., "Signal Transduction in Smooth Muscle Historical perspective on airway smooth muscle: the saga of a frustrated cell," J Appl Physiol, 2001, 91, 938-952.
Shesterina M. V., et al., "Effect of laser therapy on immunity in patients with bronchial asthma and pulmonary tuberculosis," 1993, 23-26.
Stephanie A.Shore, "Airway Smooth Muscle in Asthma—Not Just More of the Same," N Engl J Med, 2004, 351 (6), 531-532.
Sterk P. J., et al., "Heterogeneity of airway hyperresponsiveness: time for unconventional, but traditional, studies," J Appl Physiol, 2004, 96, 2017-2018.
Toma, et al., "Brave new world for interventional bronchoscopy," Thorax, 2005, 60, 180-181.
Trow T., "Clinical Year in Review I Diagnostic Imaging, Asthma, Lung Transplantation, and Interventional Pulmonology," Proceedings of the American Thoracic Society, 2006, 3, 553-556.
UNSW Embryo—Respiratory System [online], Embryology, 2007, [retrieved on Dec. 10, 2007]. Retrieved from the internet: (URL:http://embryology.med.unsw.edu.au/Refer/respire/sclect.htm).
Vasilotta P. L., et al., "I-R Laser: A new therapy in Rhino-Sino-Nasal bronchial syndrome with asthmatic component," American Society for Laser medicine and Surgery abstracts, 74.
Vorotnev, et al., "Low energy laser treatment of chronic obstructive bronchitis in a general rehabilitation center,ISSN: 0040-3660," Terapevticheskii Arkhiv, 1997, 69 (3), 17-19.
Wayne Mitzner, "Airway Smooth Muscle the appendix of the Lung," American Journal of Respiratory and Critical Care Medicine, 2004, 169, 787-790.
Wayne Mitznerl, "Bronchial Thermoplasty in Asthma," Allergology International, 2006, 55, 225-234.
Wiggs B. R., et al., "On the Mechanism of Mucosal Folding in Normal and Asthmatic Airways," J. Appl. Physiol., 1997, 83 (6), 1814-1821.
Wilson S. R., et al., "Global assessment after bronchial thermoplasty: the patients perspective," Journal of Outcomes Research, 2006, 10, 37-46.
Wizeman, et al., "A Computer Model of Thermal Treatment of Airways by Radiofrequency (RF) Energy Delivery, American Thoracic Society Annual Meeting," 2007, 1 page.

* cited by examiner

METHOD FOR TREATING AN ASTHMA ATTACK

CROSS REFERENCE TO RELATED APPLICATIONS

The present application is a continuation of U.S. patent application Ser. No. 12/727,156, filed Mar. 18, 2010, now U.S. Pat. No. 8,161,978, which is a continuation of U.S. patent application Ser. No. 11/117,905, filed Apr. 29, 2005, now U.S. Pat. No. 7,740,017 which is:

(a) a continuation application of U.S. application Ser. No. 09/999,851, filed Oct. 25, 2001, now U.S. Pat. No. 7,027,869, which is a continuation-in-part application of U.S. application Ser. No. 09/296,040, filed Apr. 21, 1999, now U.S. Pat. No. 6,411,852, each of which is herein incorporated by reference in their entirety;

(b) a continuation-in-part application of U.S. application Ser. No. 09/436,455, filed Nov. 8, 1999, now U.S. Pat. No. 7,425,212, which is incorporated by reference herein in its entirety; and (c) a continuation-in-part application of 10/232,909, filed on Aug. 30, 2002, now U.S. Pat. No. 7,556,624, which is a continuation of U.S. Application Ser. No. 09/349,715, filed Jul. 8, 1999, now U.S. Pat. No. 6,488,673, each of which is herein incorporated by reference in their entirety.

U.S. application Ser. No. 09/999,851, now U.S. Pat. No. 7,027,869, is also a continuation-in-part application of U.S. application Ser. No. 09/535,856, filed on Mar. 27, 2000, now U.S. Pat. No. 6,634,363, which is also incorporated herein by reference in its entirety.

The present application is related to U.S. application Ser. No. 09/095,323 filed Jun. 10, 1998, now abandoned; U.S. application Ser. No. 09/260,401 filed on Mar. 1, 1999, now U.S. Pat. No. 6,283,988; U.S. application Ser. No. 09/003,750 filed Jan. 7, 1998, now U.S. Pat. No. 5,972,026; and U.S. application Ser. No. 08/833,550 filed Apr. 7, 1997, now U.S. Pat. No. 6,273,907 B1, the entireties of which are incorporated herein by reference.

BACKGROUND

Asthma is a serious chronic condition affecting an estimated 10 million Americans. Asthma is characterized by (i) bronchoconstriction, (ii) excessive mucus production, and (iii) inflammation and swelling of airways. These conditions cause widespread and variable airflow obstruction thereby making it difficult for the asthma sufferer to breathe. Asthma further includes acute episodes or attacks of additional airway narrowing via contraction of hyper-responsive airway smooth muscle. Other obstructive diseases such as COPD may also have a reversible component caused by one or more of the above mentioned three elements.

Asthma generally includes excessive mucus production in the bronchial tree. Usually, there is a general increase in bulk (hypertrophy) of the large bronchi and chronic inflammatory changes in the small airways. Excessive amounts of mucus are found in the airways and semisolid plugs of mucus may occlude some small bronchi. Also, the small airways are narrowed and show inflammatory changes. The reversible aspects of COPD include partial airway occlusion by excess secretions, and airway narrowing secondary to smooth muscle contraction, bronchial wall edema and inflammation of the airways.

In asthma, chronic inflammatory processes in the airway play a central role in increasing the resistance to airflow within the lungs. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Asthma is managed pharmacologically by: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management. Thus, current management techniques are neither completely successful nor free from side effects.

In view of the foregoing, a non-pharmacological asthma treatment which does not rely on avoiding stimuli is desirable.

SUMMARY OF THE INVENTION

The invention is a method for treating lung disease and in particular, a method for treating the lung during an acute episode of reversible obstructive pulmonary disease such as an asthma attack. One embodiment of the present invention includes a method for treating asthma comprising the step of transferring energy to an airway wall of an airway in a lung such that a diameter of the airway is increased. The energy may be transferred to the airway wall prior to, during or after an asthma attack. The energy may also be transferred in an amount sufficient to temporarily or permanently increase the effective diameter of the airway. The method may be performed while the airway is open, closed or partially closed.

In another embodiment of the invention, a method for treating asthma in a lung having a constricted airway comprises transferring energy to an airway wall of the constricted airway sufficient to open the airway. The energy transferred may be in an amount sufficient to permanently or temporarily open the constricted airway. The method may be performed to open a wholly constricted airway as well as a partly constricted airway.

In yet another variation of the invention, a method for treating lung disease comprises transferring energy to an airway wall to alter the airway wall in such a manner that a resistance to airflow of the airway is decreased. The method may be performed by transferring energy to increase the caliber of the airway. The airway wall may also be altered by decreasing a thickness of the airway wall. The energy may be transferred to the airway wall during an asthma attack.

In another variation of the invention, the method comprises manipulating a distal portion of an energy delivery apparatus to a first location along the airway prior to applying the energy. The energy delivering apparatus can include a rounded tip sufficiently flexible such that when the tip encounters a closed or partially closed airway, trauma to the airway is minimized. The energy is then applied to a discrete location while the distal portion of the energy delivery apparatus is stationary. The distal portion can then be moved to a new location and the process repeated until a number of discrete locations have been treated. In an alternative, the method comprises moving the distal portion of the energy delivery apparatus from the first location and applying energy while the distal portion is being moved in the airway.

In another variation of the present invention, a method comprises transferring energy to or from an airway wall to treat a lung disease such as asthma. The method may be carried out by inserting into the airway an apparatus having a cryogenic tip or other cooling means capable of transferring energy from the tissue, resulting in a desired condition such as a larger diameter airway.

In yet another variation of the invention, a combination of the above discussed techniques are carried out such that at one time, energy is applied while the distal portion of the energy delivery device is being moved and at another time, energy is applied when the distal portion of the apparatus is stationary.

BRIEF DESCRIPTION OF THE DRAWINGS

The invention will now be described in greater detail with reference to the various embodiments illustrated in the accompanying drawings wherein.

DETAILED DESCRIPTION

This invention relates to methods for improving airflow through the airways of a lung having reversible obstructive pulmonary disease. In accordance with the invention an airway may be treated during an acute episode of reversible obstructive pulmonary disease such as an asthma attack. The invention comprises applying or transferring energy to an airway wall to increase the diameter of the airway or otherwise reduce resistance to airflow through the airway. The energy may be transferred in an amount sufficient to temporarily or permanently increase the diameter of the airway. Notably, the method may be performed while the airway is open, closed or partially closed. The inventive method thus can "rescue" an asthma sufferer during an acute asthma episode by increasing the diameter of a constricted airway.

Figure 1:
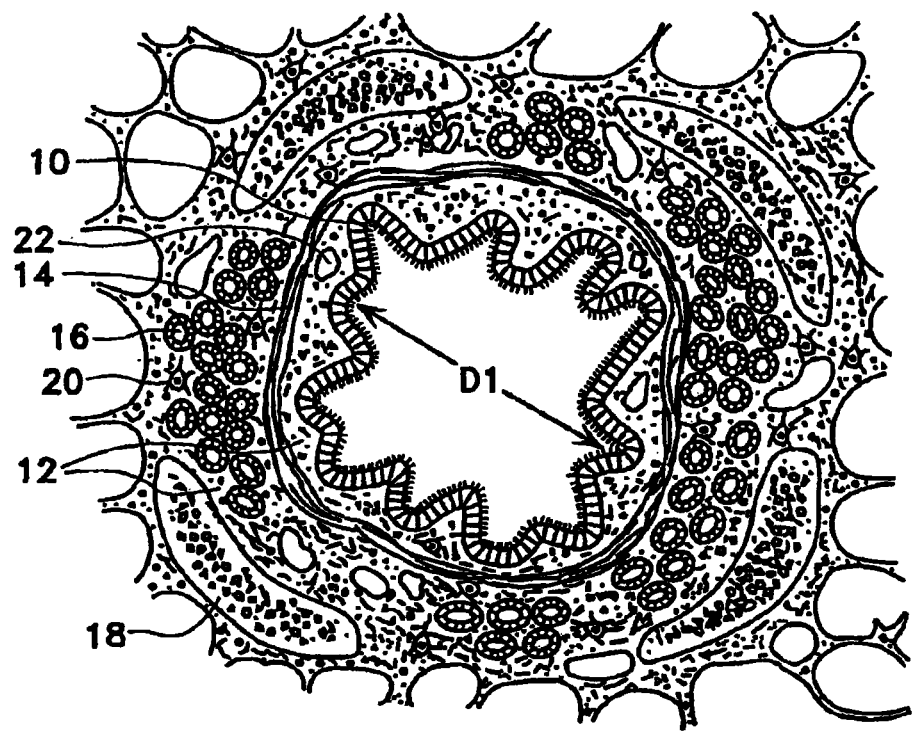
FIG. 1. is a cross sectional view of an airway in a healthy lung.
Figure 2:
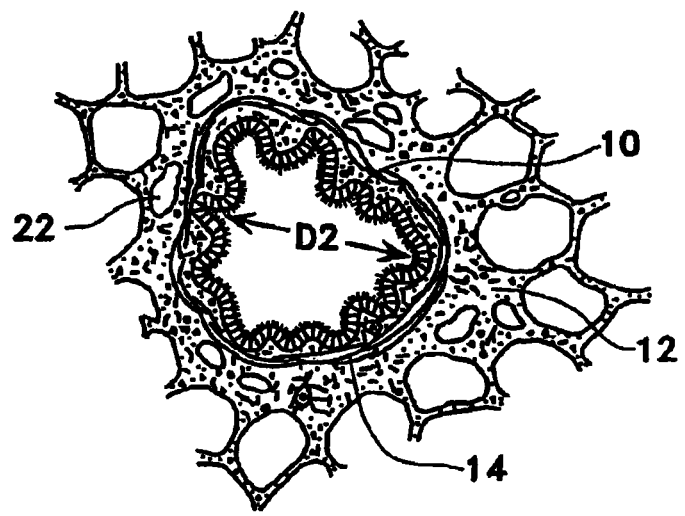
FIG. 2. shows a section through a bronchiole having an airway diameter smaller than that shown in FIG. 1.
Figure 3:
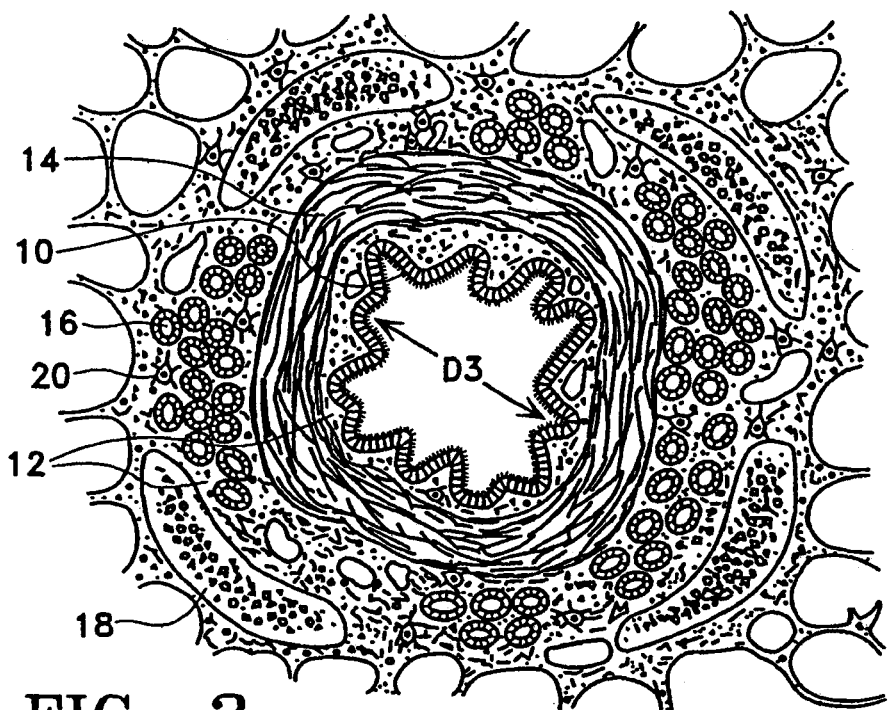
FIG. 3 illustrates the airway of FIG. 1 in which the smooth muscle has hypertrophied and increased in thickness causing reduction of the airway diameter.

Various airways are shown in FIGS. 1-3. FIGS. 1 and 2 show a cross section of two different airways in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 12 and smooth muscle tissue 14. The airway is thus quite different from other tissues such as blood vessel tissue which does not include such folds. The larger airways including the bronchus shown in FIG. 1 also have mucous glands 16 and cartilage 18 surrounding the smooth muscle tissue 14. Nerve fibers 20 and blood vessels 24 surround the airway.

FIG. 3 illustrates the bronchus of FIG. 1 in which the smooth muscle 14 has hypertrophied and increased in thickness causing the airway diameter to be reduced from the diameter D1 to a diameter D3. Accordingly, the airways to be treated with the device of the present invention may be 1 mm in diameter or greater. The airways to be treated are often second to eighth generation, and more preferably airways of the second to sixth generation.

Figure 4:
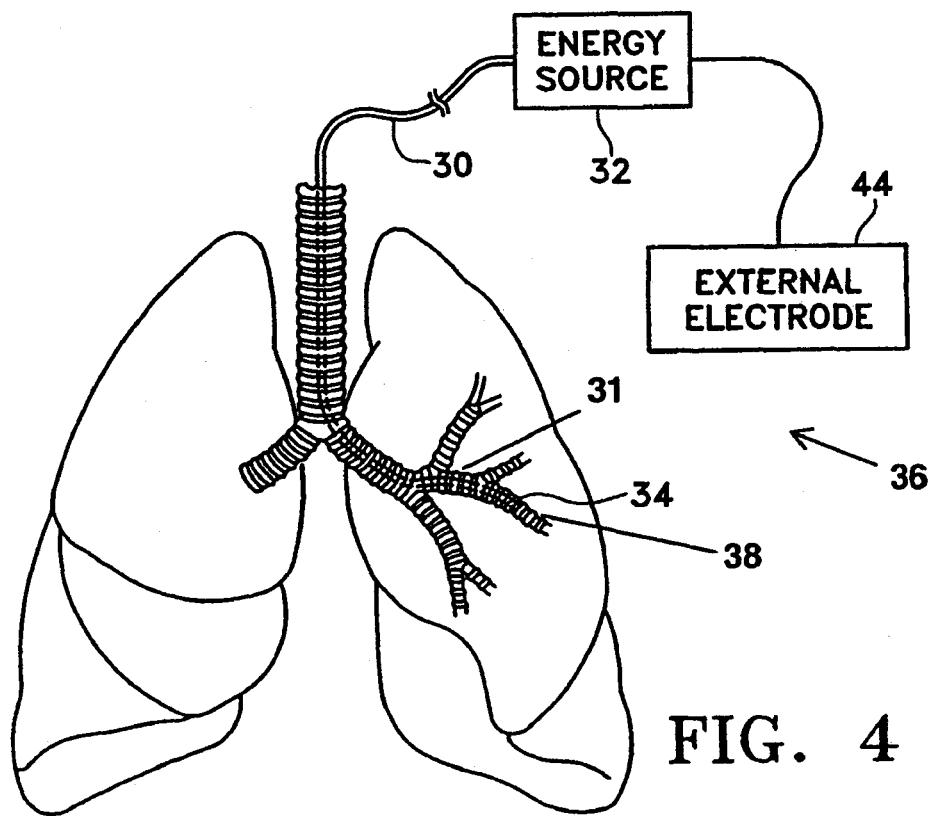
FIG. 4 is a schematic side view of the lungs being treated with a treatment device as described herein.

FIG. 4 is an illustration of the lungs being treated with a system 36 which can be used to carry out the present invention. The system 36 includes a controller 32 and an energy treatment device 30 which may be an elongated member as described further below. The device 30 also includes an expandable distal section which can be positioned at a treatment site 34 within a lung or another target medium. In operation, the device is manipulated to the treatment site 34. RF energy, for example, is delivered through the energy delivering device and penetrates the surface of the lung tissue such that tissue is affected below the epithelial layer as well as on the surface of the lung tissue. The application of energy may cause a variety of structural and physiological effects which may result from the application of energy to the airway wall. For example, application of energy to the airway smooth muscle of an asthmatic patient can debulk or otherwise reduce the volume of smooth muscle. This reduced volume of smooth muscle increases the airway diameter for improved air exchange. Even small increases in the airway size can provide relief as the resistance to airflow varies inversely with approximately the fourth power of diameter.

Application of energy to an airway wall can also reduce inflammation in the inner lung tissue. Reducing inflammation and edema of the tissue surrounding the airway can increase the diameter of an airway. Inflammation and edema (accumulation of fluid) of the airway are chronic features of asthma. The inflammation and edema can be reduced by application of energy to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. The wound healing can also deposit collagen which improves parenchymal tethering.

Application of energy to an airway wall can also inhibit the release of inflammatory mediators in the airway wall which may serve as a stimulus for airway smooth muscle contraction. Therapy that reduces the production and release of inflammatory mediators can reduce smooth muscle contraction, inflammation of the airways, and edema. Examples of inflammatory mediators are cytokines, chemokines, and histamine. The tissues which produce and release inflammatory mediators include airway smooth muscle, epithelium, and mast cells. Thus, treatment of these structures with energy can reduce the ability of the airway structures to produce or release inflammatory mediators. The reduction in released inflammatory mediators will reduce chronic inflammation, thereby increasing the airway inner diameter, and may also reduce hyper-responsiveness of the airway smooth muscle.

Application of energy to an airway wall can also increase the airway diameter by damaging nerve tissue in the airways. This follows because a resting tone of smooth muscle is nerve regulated by release of catecholamines. Thus, by damaging or eliminating nerve tissue in the airways the resting tone of the smooth muscle is reduced, and the airway diameter is increased.

Application of energy to the airways may cause other physiological responses which result in increased diameters. It is to be understood, however, that the invention is not limited to a certain physiological response or process except where such a physiological response or process is a claim limitation in the appended claims.

As shown in FIG. 4, the present invention may be performed using a controller 32 and a device 30 through which it delivers energy to the target medium 34. A device 30 of the present invention should be of a size to access the bronchus or bronchioles of the human lung. The device may be sized to fit within bronchoscopes, preferably, with bronchoscopes having a working channel of 2 mm or less. The device may also include a steering member configured to guide the device to a desired target location. For example, this steering member may deflect a distal tip of the device in a desired direction to navigate to a desired bronchi or bronchiole.

Another aspect of the present invention is to treat more than one location. Several to many locations (e.g., reference numerals 31, 34 and 38) in the airways may be treated in order to reduce asthmatic symptoms. This can be accomplished by manipulating or positioning the expandable basket at a target site in the airways, expanding the expandable basket such that the energy transfer elements (e.g., the basket legs) contact the airway wall, and then delivering energy to the airway wall. The expandable basket is preferably collapsed and moved to another location and the process is repeated. This technique for applying energy at discrete locations can be repeated as many times as necessary to treat the asthmatic symptoms.

The present invention also includes applying energy continuously along an airway as an expanded basket is moved along the airway. Specifically, the basket may be deployed, energized, and then moved along the airway continuously to continually transfer energy to or from the airway wall as the basket is moved axially along the airway. The above described methods may also be used in combination with one another.

Figure 5:
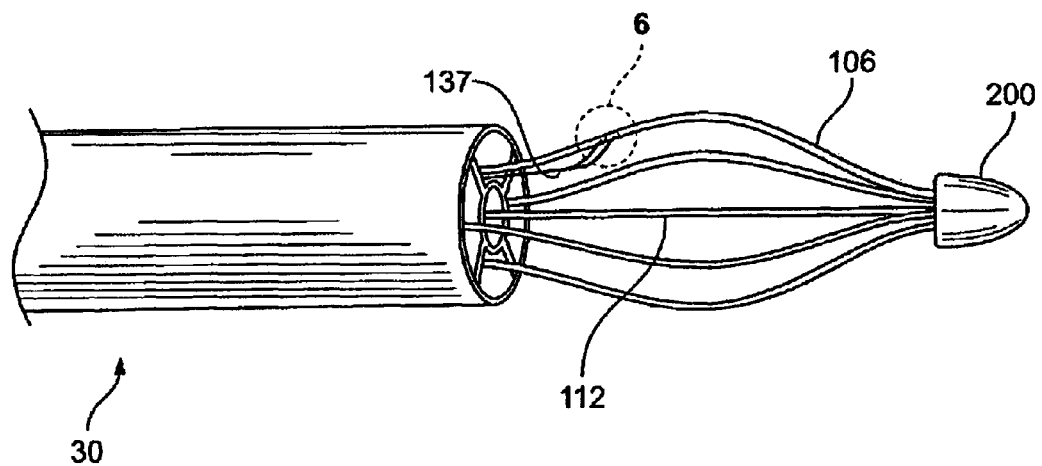
FIG. 5 is a partial view of an energy delivery device which can be used to carry out the method of the invention.

An exemplary partial view of an energy delivering device which may be used to perform the invention is shown in FIG. 5. The energy delivering apparatus 30 typically includes an elongate body having a proximal section and a distal section. The distal section features a radially expandable basket having a plurality of legs 106. The legs may be electrodes or have an active region defined by an insulated covering which contacts the medium to be treated. The basket is expanded with an actuator mechanism 112 which may be activated by a movable lever in a handle attached to the proximal end of the elongate body.

The invention may also include an atraumatic tip 200 to ensure that the invention does not injure airway tissue when it is placed into airways that are partially or completely closed. The tip may be formed of a flexible material and/or may be rounded to minimize trauma. Examples of energy delivering devices in accordance with the present invention are described in co-pending U.S. application Ser. No. 09/436,455 filed Nov. 8, 1999 which is hereby incorporated by reference in its entirety. Other examples of devices and methods which may be used in accordance with the present invention are found in the following U.S. patent applications: Ser. No. 09/095,323—Methods and Apparatus for Treating Smooth Muscles in the Walls of Body Conduits; Ser. No. 09/349,715—Method of Increasing Gas Exchange of a Lung; and Ser. No. 09/296,040—Devices for Modification of Airways By Transfer of Energy. The entirety of each of the aforementioned applications is hereby incorporated by reference. Another suitable energy device is described in International patent application no PCT/US00/28745.

The energy delivery device may further comprise a temperature detecting element. Examples of temperature detecting elements include thermocouples, infrared sensors, thermistors, resistance temperature detectors (RTDs), or any other apparatus capable of detecting temperatures or changes in temperature. The temperature detecting element is preferably placed in proximity to the expandable member.

Figure 6:
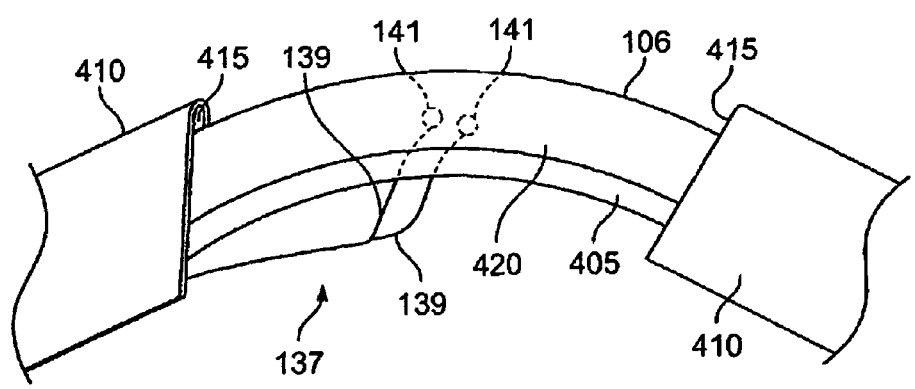
FIG. 6 is a partial view of a thermocouple attached to an energy delivering device in accordance with the invention.

FIG. 5 is a partial view of a variation of the energy delivery device having thermocouple 137 positioned about midway along basket leg 106. FIG. 6 is an enlarged partial view of the thermocouple 137 of FIG. 5 showing the leads 139 separately coupled on an inwardly-facing surface of the leg 106. Consequently, the basket leg itself is used as part of the thermocouple junction upon which the temperature measurement is based. The thermocouple junction is intrinsic to the basket leg. This configuration is preferred because it provides an accurate temperature measurement of tissue contacting the leg 106 in the vicinity of the thermocouple leads. In contrast, typical thermocouple configurations consist of a thermocouple junction offset or extrinsic to the basket leg. Thermocouple junctions offset or extrinsic to the basket leg do not measure temperature as accurately in certain applications as thermocouple junctions which are intrinsic to the basket leg.

An intrinsic thermocouple junction configuration is safer than an extrinsic thermocouple junction because, in the event one of the thermocouple leads separates from a basket leg, the intrinsic thermocouple junction becomes "open" and no thermocouple signal is produced. In contrast, when an extrinsic thermocouple junction separates from a basket leg a signal continues to be produced. The signal of a detached extrinsic thermocouple junction can be misleading because although a temperature reading continues to be produced, the temperature reading does not reflect the temperature at the point where the basket leg contacts the subject tissue. Accordingly, an intrinsic thermocouple junction having two leads separately attached to a basket leg is preferred.

FIG. 6 also shows basket leg 106 having an outer insulating material or coating 410. The boundaries 415 of the insulating material 410 define an uninsulated, active section of electrode leg 106 which delivers energy to the airway walls. Preferably, the insulating coating 410 is heat shrink tubing or a polymeric coating. However, other insulating materials may be used.

Various controllers may be used to carry out the invention. An example of an RF controller which may be used to carry out the invention is described in co-pending International Patent Application No. PCT (not yet assigned), entitled "CONTROL SYSTEM AND PROCESS FOR APPLICATION OF ENERGY TO AIRWAY WALLS AND OTHER MEDIUMS" filed Oct. 17, 2001 incorporated herein by reference in its entirety.

The controller and power supply is configured to deliver enough energy to produce a desired effect in the lung. The power supply should also be configured to deliver the energy for a sufficient duration such that the effect persists. This may be accomplished by a time setting which may be entered into the power supply memory by a user.

The power supply or generator may also employ a number of algorithms to adjust energy delivery, to compensate for device failures (such as thermocouple detachment), to compensate for improper use (such as poor contact of the electrodes), and to compensate for tissue inhomogeneities which can affect energy delivery such as, for example, subsurface vessels, adjacent airways, or variations in connective tissue.

The power supply can also include circuitry for monitoring parameters of energy transfer: (for example, voltage, current, power, impedance, as well as temperature from the temperature sensing element), and use this information to control the amount of energy delivered. In the case of delivering RF energy, typical frequencies of the RF energy or RF power waveform are from 300 to 1750 kHz with 300 to 500 kHz or 450 to 475 being preferred. The RF power-level generally ranges from about 0-30 W but depends upon a number of factors such as the size and number of the electrodes. The controller may also be configured to independently and selectively apply energy to one or more of the basket leg electrodes.

A power supply may also include control modes for delivering energy safely and effectively. Energy may be delivered in open loop (power held constant) mode for a specific time duration. For example, a power setting of 8 to 30 Watts for up to 10 seconds is suitable and a power setting of 12 to 30 Watts for up to 5 seconds is preferred. For more permanent restructuring of the airways, a power setting of 8 to 15 Watts for 5 to 10 seconds is suitable. For mere temporary relief or enlargement of the airway, a power setting of 10 to 25 Watts for up to 3 seconds is suitable. With higher power settings, correspondingly lower time durations are preferred to limit collateral thermal damage.

Energy may also be delivered in temperature control mode, with output power varied to maintain a certain temperature for a specific time duration. For example, energy may be delivered for up to 20 seconds at a temperature of 55 to 80 degrees C., and more preferably, energy is delivered up to 10 seconds at a temperature in the range of 60 to 70 degrees C. For more permanent restructuring of the airways, energy is delivered for 5 to 10 seconds at a temperature in the range of 60 to 70 degrees C. For mere temporary relief or enlargement of the airway, energy is delivered for up to 5 seconds at a temperature of 55 to 80 degrees C. Additionally, the power supply may operate in impedance control mode.

The operator may start at low values of power, temperature and time, and treat until the desired effect (for example, airway diameter increasing or tissue blanching) is acutely observed, raising the power, temperature or time as needed.

Notably, the methods of the invention may be performed while the lung is experiencing natural symptoms of reversible obstructive pulmonary disease. One such example is where an individual, experiencing an asthma attack, or acute exacerbation of asthma or COPD, undergoes treatment to improve the individual's ability to breath. In such a case, the treatment provides immediate relief for (i.e., "rescues") the patient.

All of the features disclosed in the specification (including any accompanying claims, abstract and drawings), and/or all of the steps of any method or process disclosed, may be combined in any combination, except combinations where at least some of such features and/or steps are mutually exclusive.

Each feature disclosed, in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method for treating a subject, the method comprising:
    moving an elongate assembly along a lumen of an airway of a bronchial tree, wherein the elongate assembly includes an expandable distal energy delivery portion having an electrically conductive region defined by an electrically nonconductive portion; and
    by delivering energy with the energy delivery portion, damaging nerve tissue of a nerve trunk extending along the airway to attenuate nervous system signals transmitted to a portion of the bronchial tree.

2. The method of claim 1, wherein damaging the nerve tissue comprises irreversibly damaging the nerve tissue to at least partially block a transmission of nervous system signals and to cause a decrease in smooth muscle tone of the portion of the bronchial tree.

3. The method of claim 1, wherein damaging the nerve tissue comprises:
    destroying a section of the nerve tissue using the delivered energy such that the destroyed section impedes transmission of nervous system signals traveling along the nerve tissue.

4. The method of claim 1, further comprising:
    terminating energy delivery;
    moving the distal energy delivery portion in the airway to a second location; and
    damaging nerve tissue at the second location.

5. The method of claim 1, wherein damaging nerve tissue comprises heating an electrode of the distal energy delivery portion to a temperature of approximately 60 to 80 degrees C.

6. The method of claim 1, wherein damaging nerve tissue reduces a resting tone of smooth muscle of the airway so as to substantially increase airflow into and out of a lung of the subject.

7. The method of claim 1, wherein damaging nerve tissue comprises decreasing a resistance to airflow within the bronchial tree.

8. The method of claim 1, wherein damaging nerve tissue comprises delivering RF energy to the airway.

9. The method of claim 1, further comprising a plurality of electrodes spaced about the distal energy delivery portion.

10. The method of claim 9, wherein the plurality of electrodes are radially spaced about the distal energy delivery portion and extend longitudinally.

11. A method for treating a subject, the method comprising:
    moving an elongate assembly along a lumen of an airway of a bronchial tree, wherein the elongate assembly includes a distal energy delivery portion having a plurality of electrodes spaced about the distal energy delivery portion; and
    by delivering energy with the energy delivery portion, damaging nerve tissue of a nerve trunk extending along the airway to attenuate nervous system signals transmitted to a portion of the bronchial tree;
    terminating energy delivery;

moving the distal energy delivery portion to a second location in the bronchial tree; and damaging nerve tissue at the second location.

12. The method of claim 11, wherein the plurality of electrodes are radially spaced about the distal energy delivery portion and extend longitudinally.

13. The method of claim 11, wherein damaging nerve tissue comprises heating the plurality of electrodes to a temperature of approximately 60 to 80 degrees C.

14. The method of claim 11, wherein damaging nerve tissue reduces a resting tone of smooth muscle of the airway so as to substantially increase airflow into and out of a lung of the subject.

15. The method of claim 11, wherein damaging nerve tissue comprises decreasing a resistance to airflow within the bronchial tree.

16. The method of claim 11, wherein damaging nerve tissue comprises delivering RF energy to the airway.

* * * * *